(12) United States Patent
Adie et al.

(10) Patent No.: US 11,480,423 B2
(45) Date of Patent: Oct. 25, 2022

(54) ABERRATION DIVERSE OPTICAL COHERENT TOMOGRAPHY (OCT) IMAGING TO SUPPRESS OPTICAL SCATTERING NOISE

(71) Applicant: Cornell University, Ithaca, NY (US)

(72) Inventors: Steven Adie, Ithaca, NY (US); Siyang Liu, Ithaca, NY (US); Michael Lamont, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 17/025,814

(22) Filed: Sep. 18, 2020

(65) Prior Publication Data

US 2021/0003382 A1 Jan. 7, 2021

Related U.S. Application Data

(63) Continuation of application No. PCT/US2019/023271, filed on Mar. 20, 2019.

(60) Provisional application No. 62/645,724, filed on Mar. 20, 2018.

(51) Int. Cl.
*G01B 9/02091* (2022.01)
*G01B 9/02055* (2022.01)
*G01N 21/49* (2006.01)
*G01B 9/02056* (2022.01)

(52) U.S. Cl.
CPC ..... *G01B 9/02082* (2013.01); *G01B 9/02058* (2013.01); *G01B 9/02091* (2013.01); *G01N 21/49* (2013.01)

(58) Field of Classification Search
CPC ............ G01B 9/02082; G01B 9/02058; G01B 9/02091; G01B 9/02041; G01B 9/02087; G01N 21/49; A61B 5/0066
See application file for complete search history.

(56) References Cited

U.S. PATENT DOCUMENTS

| 4,865,454 | A | 9/1989 | Lazzarini et al. |
| 6,470,124 | B1 | 10/2002 | Le Gargasson et al. |
| 7,791,734 | B2 * | 9/2010 | Olivier ................... A61B 3/102 356/479 |
| 2002/0010593 | A1 | 8/2002 | Yang et al. |
| 2009/0040527 | A1 | 2/2009 | Popescu et al. |
| 2013/0107268 | A1 | 5/2013 | Boccara |
| 2014/0050382 | A1 | 2/2014 | Adie et al. |

(Continued)

OTHER PUBLICATIONS

The International Search Report, dated May 16, 2019 in connection with PCT International Application No. PCT/US2019/023271, 11 pages.

(Continued)

*Primary Examiner* — Jonathan M Hansen
(74) *Attorney, Agent, or Firm* — Perkins Coie LLP

(57) ABSTRACT

The technology disclosed in this patent document can be used to implement an optical coherent tomography (OCT) system that combines a control of the probe light to the target sample with different optical aberration patterns in optically probing the target sample and an OCT imaging processing to enhance the OCT imaging quality by combining image signals from in-phase contributions from the probing with different optical aberration patterns while suppressing randomly phased contributions from scattering by the target sample.

20 Claims, 9 Drawing Sheets

(56) References Cited

U.S. PATENT DOCUMENTS

2014/0118695 A1* 5/2014 Shimada ................ A61B 3/102
351/206
2016/0067086 A1 3/2016 Tedford et al.

OTHER PUBLICATIONS

She, A., et al, "Adaptive metalenses with simultaneous electrical control of focal length, astigmatism, and shift," Science Advances, Feb. 23, 2018, vol. 4, No. 2, eaap9957, 8 pages.

* cited by examiner

ABERRATION DIVERSE OPTICAL COHERENT TOMOGRAPHY (OCT) IMAGING TO SUPPRESS OPTICAL SCATTERING NOISE

PRIORITY CLAIMS AND RELATED PATENT APPLICATIONS

This patent document is a continuation application of, and claims the priority and benefits of, PCT Application No. PCT/US2019/023271 entitled "ABERRATION DIVERSE OPTICAL COHERENCE TOMOGRAPHY (OCT) IMAGING TO SUPPRESS OPTICAL SCATTERING NOISE" and filed on Mar. 20, 2019, which further claims the priority and benefits of U.S. Provisional Patent Application No. 62/645,724 entitled "ABERRATION DIVERSE OPTICAL COHERENT TOMOGRAPHY (OCT) IMAGING TO SUPPRESS OPTICAL SCATTERING NOISE" and filed on Mar. 20, 2018. The entire contents of the above applications are incorporated by reference as part of the disclosure of this patent document.

TECHNICAL FIELD

This patent document relates to optical imaging of tissues and other objects.

BACKGROUND

Optical Coherent Tomography (OCT) imaging is based on optical interference of a reference optical beam and a probe or sampling optical beam that interacts with a target such as a tissue to obtain imaging information and to extract one or more properties of the target. OCT cam be implemented in the time-domain OCT or spectral or frequency domain OCT. OCT devices can be used to provide non-invasive and label-free optical imaging of tissues and other objects or structures at a high resolution and can be implemented to provide optical imaging on the cellular scale.

SUMMARY

The technology disclosed in this patent document relates to optical imaging of tissues and other objects.

Various OCT applications are limited in their imaging penetration depths, e.g., on the order of a millimeter in tissue, and this limitation in the imaging depths worsens in highly scattering media where detected multiple scattering contributions can increase the image background significantly. The OCT technology disclosed in this document combines a control of the probe light to the target sample with different optical aberration patterns in optically probing the target sample and an OCT imaging processing to enhance the OCT imaging quality by combining image signals from in-phase contributions from the probing with different optical aberration patterns while suppressing randomly phased contributions from scattering by the target sample.

In one implementation, for example, an optical coherent tomography (OCT) device for optically measuring a target sample can be constructed based on the disclosed technology to include: a light source to direct probe light to the target sample to collect returned probe light from the target sample to perform OCT imaging; an optical aberration device placed in an optical path of the probe light upstream (e.g., backscattered probe light) from the target sample and structured to sequentially superimpose different optical aberration patterns on the wavefront of the probe light directed to the target sample to obtain different OCT imaging outputs, respectively, that respectively correspond to the different optical aberration patterns; an OCT processor coupled to the light source to receive the different OCT imaging outputs that respectively correspond to the different optical aberration patterns and to process the received different OCT imaging outputs to reconstruct different OCT images of the target sample, respectively, where each reconstructed OCT image corresponds to one of the different OCT imaging outputs and includes (1) first OCT image components that are caused by ballistic photons of the probe light with a single-scattering contribution and are in phase and (2) second OCT image components that are caused by scattered photons of the probe light due to scattering in the target sample and exhibit random phase values.

In this OCT device, the OCT processor is further configured to add the reconstructed OCT images together to obtain a final reconstructed OCT image based on a first sum of the first OCT image components of the different reconstructed OCT images that are in phase and a second sum of the second OCT image components of the different reconstructed OCT images exhibiting random phase values, thus suppressing a contribution of the second sum caused by scattered photons of the probe light due to scattering in the target sample.

In another aspect, for example, the disclosed technology can be implemented to provide a method for optically measuring a target sample based on OCT imaging. The method includes: operating a light source to direct probe light to the target sample and to collect returned probe light from the target sample to perform OCT imaging; sequentially superimposing different optical aberration patterns on the wavefront of the probe light directed to the target sample to obtain different OCT imaging outputs, respectively, that respectively correspond to the different optical aberration patterns; processing the different OCT imaging outputs that respectively correspond to the different optical aberration patterns to reconstruct different OCT images of the target sample, respectively, where each reconstructed OCT image corresponds to one of the different OCT imaging outputs and includes (1) first OCT image components that are caused by ballistic photons of the probe light with a single-scattering contribution and are in phase and (2) second OCT image components that are caused by multiply scattered photons of the probe light due to multiple scattering in the target sample and exhibit random phase values; and subsequently adding the reconstructed OCT images together to obtain a final reconstructed OCT image based on a first sum of the first OCT image components of the different reconstructed OCT images that are in phase and a second sum of the second OCT image components of the different reconstructed OCT images exhibiting random phase values, thus suppressing a contribution of the second sum caused by multiply scattered photons of the probe light due to multiple scattering in the target sample.

DETAILED DESCRIPTION

Figure 1:
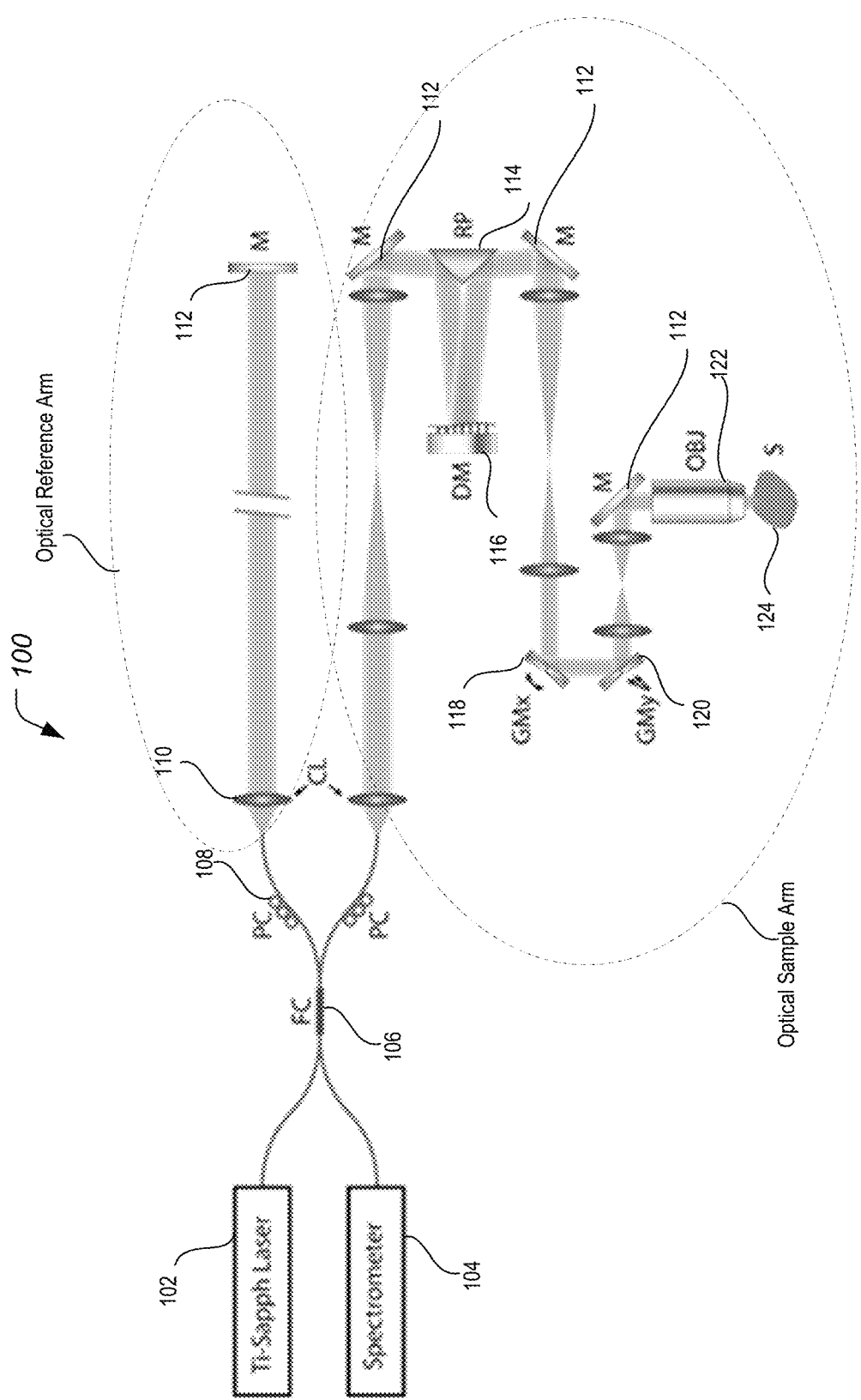
FIG. 1 shows an example system diagram for hybrid adaptive optics (AO) optical coherence microscopy (OCM).

Disclosed are devices, systems and methods for optical imaging of tissues and other objects.

Optical coherence tomography (OCT) can be a powerful imaging tool used both in the clinic and for basic biological research in the laboratory. When properly implemented, an OCT measurement is non-invasive, label-free, and capable of high resolution on the cellular scale. However, OCT is limited in its penetration depth, typically a millimeter in tissue, and this problem worsens in highly scattering media where detected multiple scattering contributions can increase the image background significantly. Mitigating the effect to the final OCT imaging by multiple scattering contributions has become the focus of many optical imaging researchers around the world.

An OCT system can be configured to include two optical arms: a reference arm that provides an optical reference signal and a sample arm with a sample to be measured. The probe light from a light source is split into a sampling beam for going into the sample arm to interact with the same and a reference beam which propagates into the reference arm as the reference signal. In some implementations, the two optical arms may spatially overlap to share a common optical path where, for example, the reference arm signal may be generated from a reflector that is placed in a common-path with the sample arm light path. The light source may be a coherent or partially coherent source. In various implementations, it is desirable that the light from the light source has a low temporal coherence where the coherence between one moment in time of a wave with another moment of time in the same wave decreases significantly over a time difference between the two moments in time and a sufficient spatial coherence which is, at a given moment in time, the coherence or partial coherence between light signals from two different locations on a wavefront. The sampling beam returned from the sample arm and the reference signal returned from the reference arm or common-path reflector in the sample arm are brought to overlap with each other to optically interfere for the OCT detection and processing. The light scattering in the sample produces different scattered photons, including ballistic photons that are scattered once in the sample and have a specific optical path length delay with respect to the reference path length and multiply scattered photons of the probe light due to multiple scattering in the target sample originating from different spatial locations than that of the ballistic light. Notably, the presence of multiply scattered photons in the OCT detection adds to the background noise in the contribution of ballistic photons to the OCT signal and thus is undesirable.

The disclosed optical coherent tomography (OCT) imaging method can be used to reduce the background due to multiple scattering and to provide full 3D volumetric dataset, is non-iterative, and may be performed on any sample. This method leverages hybrid adaptive optics (hyAO) platform, taking advantage of hardware adaptive optics (HAO) to introduce an astigmatic wavefront aberration and computational adaptive optics (CAO) to undo this aberration during post-processing.

Various embodiments of the disclosed technology implemented to reduce the multiple scattering background can take advantage of the complex OCT signal obtained. Consider a voxel with a phase-stable signal resulting from a single scattering event. If N measurements of this voxel can be taken, the resulting complex valued signal S remains constant, and the summed amplitude grows by a factor of N. Now consider a voxel containing a noisy background, B, with a randomly fluctuating phase. Adding the complex background of N measurements can be considered analogous to a random-walk across the complex plane, so the summed magnitude would grow at a rate of the square root of N. By adding N volumetric datasets containing phase-stable signals and randomly fluctuating background, therefore, an ideal signal-to-background ratio (SBR) improvement of the square root of N over the SBR of a single dataset can be expected.

This patent document provides various ways to randomize the phase of multiple scattering contributions between each volume in implementing the OCT device.

Some embodiments of the disclosed technology take advantage of the flexibility offered by hyAO to create an astigmatic interrogating wavefront for the measurement and correct this aberration in post-processing. For each dataset, the optical aberration (e.g., the astigmatism) is rotated slightly, which causes little change to the phase of single scattered signals reconstructed by CAO. However, it can drastically alter the beam path within the sample and thus the phase of any multiple scattering contributions. This method of aberration diverse OCT (AD-OCT) can be implemented in various ways, including a spectral domain OCT (SD-OCT) system outfitted with a deformable mirror to apply known astigmatic wavefronts. Various devices can be used to replace the deformable mirror, allowing precise control of the optical astigmatism and other optical aberrations, aberration-diverse astigmatic illumination, for example, using a cylindrical lens. For example, such a precise control of astigmatism and other aberrations, aberration-diverse astigmatic illumination may also be achieved by simply adding a cylindrical lens on a rotating mount.

FIG. 1 shows an example system diagram for hybrid adaptive optics (AO) optical coherence microscopy (OCM). The top part shows the optical reference arm and the lower part shows the optical sample arm. The hybrid AO OCM implemented based on some embodiments of the disclosed technology may include a light source 102, a spectrometer 104, a fiber coupler 106, polarization controllers 108, collimating lenses 110, mirrors 112, a deformable mirror 114, a right-angle prism 110, galvanometer mirrors along x and y directions (GMx and GMy) 118 and 120, an objective lens 122. Additionally, telescope lenses may be used for pupil conjugation.

In one example of an OCT based on a SD-OCT system with adaptive optics, the system is illuminated by a Ti:S sapphire broadband laser source (e.g., femtolasers) with 810 nm central wavelength and 150 nm bandwidth. In the sample arm, the plane of the deformable mirror 116 is conjugate to the entrance pupil of the objective lens 122 to shape the wavefront. The midpoint of the (coupled) X-scan and Y-scan galvanometer mirrors 118 and 120 is conjugate to the back focal plane of the objective lens 122 to minimize the scan path variation, described as coherence gate curvature. After the sample arm signal is superimposed with a reference arm signal at the fiber coupler 106 (e.g. 50:50 coupler), the net signal is collected by the spectrometer 104 (e.g. spectrometer with a 12-bit line scan camera). The laser and spectrometer combination can offer a 2 µm full-width-at-half-maximum (FWHM) axial resolution. The total incident power on a sample 124 may be measured to be 23 mW, yielding a peak imaging sensitivity of 94 dB at 300 µm below zero optical path delay (with a 5 dB/mm sensitivity fall-off). The hybrid adaptive optics (hyAO) method may be first validated via bead phantom (TiO2 in silicone) imaging by quantifying the depth-dependent SNR and resolution. Then, the technique is applied to imaging in a grape to demonstrate its advantage in imaging cellular structure.

Tests may be conducted by using the hybrid adaptive optics (hyAO) approach to capture a 1 mm×1 mm×1 mm FOV within a sample (e.g., Matrigel) containing live NIH-3T3 fibroblast cells to demonstrate the capability of the technique to perform high-throughput in vitro cell imaging.

The deformable mirror is used to physically adjust the optical aberration level (e.g., the astigmatism level) and the corresponding separation distance between line foci. If a single axial beam position is inadequate to acquire an OCM volume with desired depth coverage, an additional amount of defocus is applied to the deformable mirror to shift the nominal focus (the plane of least confusion in the case of the astigmatic beam), to acquire multiple datasets with the plane of least confusion at different depths. In post-processing, the resolution penalty of defocus and the intentionally applied astigmatism may be compensated with CAO. In addition to the recovery of spatially invariant focal-plane resolution, this may also result in an improvement of SNR associated with the restoration of constructive interference via CAO.

In some implementations, a measurement data set obtained by the hybrid AO OCM may include a number of volumetric OCT measurements (e.g., 100 volumetric OCT measurements) taken with an astigmatic interrogating beam, rotating the astigmatic state 1=100th of a complete rotation (e.g., 180°) between each volume. Before imaging a highly scattering sample, a system calibration step may be required to find the necessary CAO parameters. This may be done using a silicone phantom with a sparse concentration of 0.1% by weight TiO2 nanoparticles. The particles may be used as "guide stars" for optimizing the Zernike polynomial coefficients of defocus, oblique and vertical astigmatism required to correct the aberrations introduced at each state in the measurement based on some embodiments of the disclosed technology. If the calibration sample is of similar refractive index to the sample of interest, only the new focus depth must be found, and all other calibration values may be retained when applying CAO. The highly scattering sample used may be another silicone phantom with a dense concentration of 1.0% by weight TiO2 nanoparticles and a thickness of 427 mm, roughly 7.1 scattering lengths.

Figure 2A:
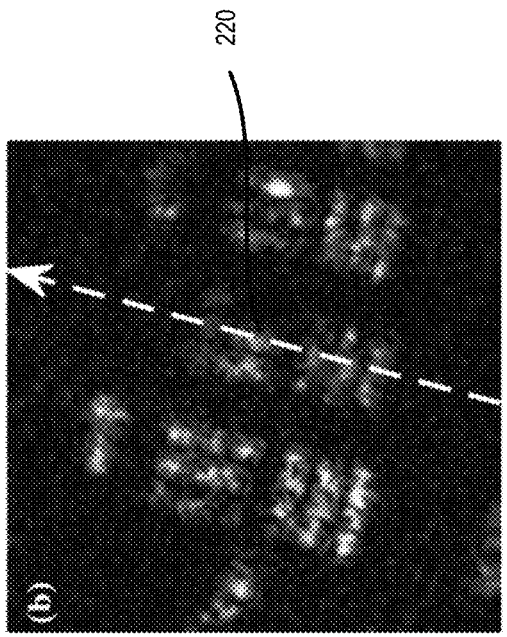
FIG. 2A shows single CAO-corrected en face image.
Figure 2B:
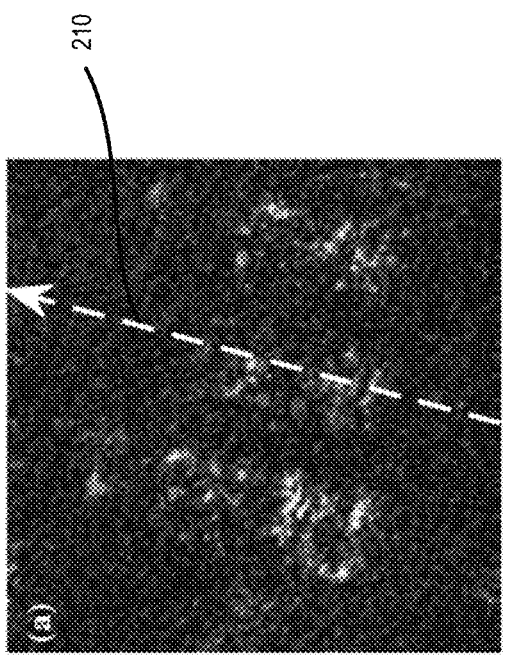
FIG. 2B shows after averaging 100 complex CAO-corrected images at different astigmatic rotations.
Figure 2C:
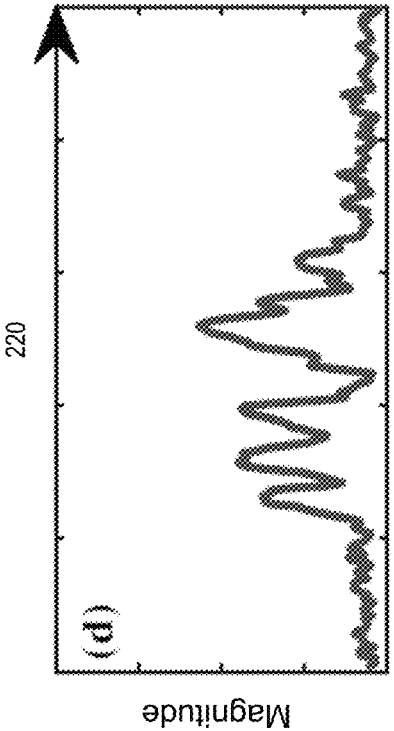
FIGS. 2C and 2D show signal magnitude along the dotted line in FIGS. 2A and 2B, same vertical scale from zero.
Figure 2D:
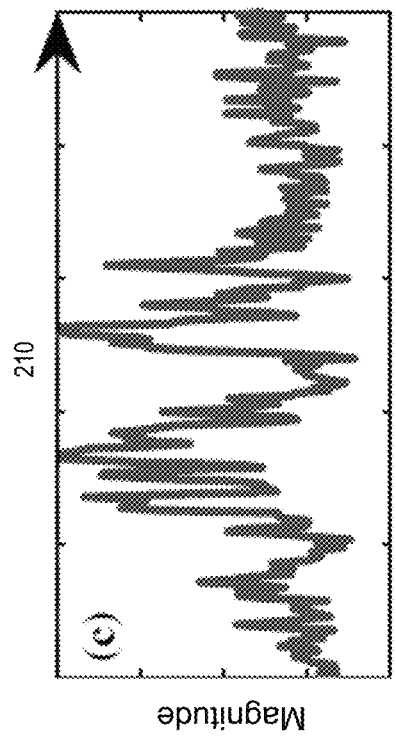
Figure 2E:
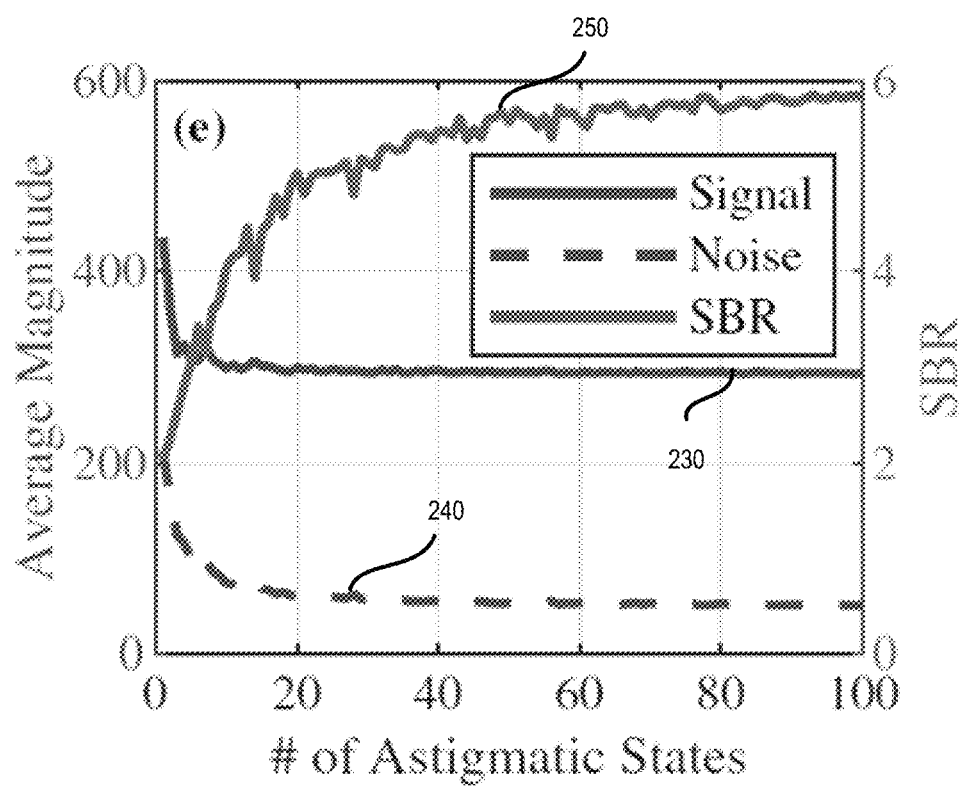
FIG. 2E shows effects of the number of astigmatic states on average image signal, background, and signal-to-background ratio (SBR).
Figure 2F:
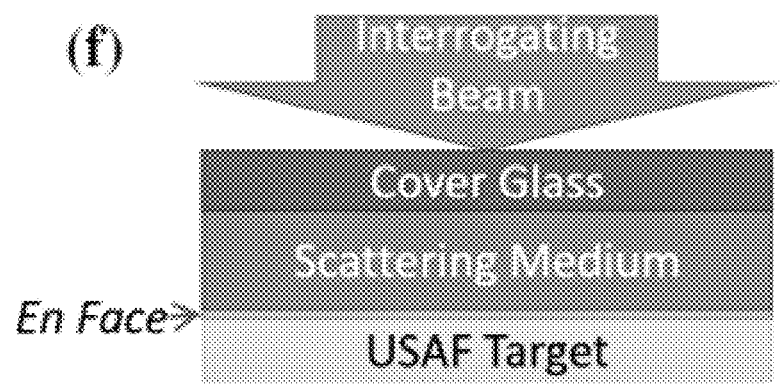
FIG. 2F shows a sample diagram.

FIG. 2A shows single CAO-corrected en face image. FIG. 2B shows after averaging 100 complex CAO-corrected images at different astigmatic rotations. FIGS. 2C and 2D show signal magnitude along the dotted line in FIGS. 2A and 2B, same vertical scale from zero. FIG. 2E shows effects of the number of astigmatic states on average image signal, background, and signal-to-background ratio (SBR). FIG. 2F shows a sample diagram.

FIG. 2A shows the signal magnitude of a typical OCT en face image, at the depth of the USAF target, after CAO reconstruction. In FIG. 2B, all 100 complex images in the dataset are averaged before taking the magnitude. This "coherent average" results in a decreased multiple scattering background. The magnitude along the dotted lines through the target images are shown in FIGS. 2C and 2D. Note that the complex values of voxels comprising the USAF image contain both single scattering as well as multiple scattering contributions. FIG. 2D shows how a coherent average reduces the background contributions to the image while maintaining the signal from the target. FIG. 2E shows how the number of aberration states used in the average affects a signal 230 and background 240 in the resulting image. The states used are near-equidistant and span a full 180° astigmatic rotation astigmatic rotation. The signal 230 is any voxel within a masking image of the bars on the USAF target. The background 240 is a plane 6 mm below the USAF target surface. Using AD-OCT coherent averaging implemented based on some embodiments of the disclosed technology, the multiple scattering contribution to both the signal and background voxels is reduced dramatically with as few as 10 states included. This results in a sharp improvement to signal-to-background ratio (SBR) 250. As shown in FIG. 2F, a 1951 USAF resolution target may be placed beneath this phantom and imaged the first three elements of the seventh group (3.91, 3.48, 3:10 mm line width, respectively). In this way, a simple and effective method of aberration diverse OCT illumination combined with coherent averaging of CAO-corrected images can be implemented to significantly reduce multiple scattering effects, which would allow deeper volumetric imaging in scattering media. AD-OCT yields improved SBR with as few as tens of images, in contrast to other methods that use as many as $10^3$ images.

The disclosed OCT technology can be used to improve optical coherence microscopy (OCM) and three photon microscopy (3PM), namely volumetric acquisition speed and imaging depth. To some extent, the disclosed OCT technology is a "hybrid adaptive optics (AO)—an imaging paradigm that synergistically combines hardware adaptive optics (HAO) and computational adaptive optics (CAO) approaches that can be utilized as mutually exclusive methods. The disclosed OCT technology can overcome the multiple scattering limit and demonstrate "super-deep" OCM in scattering biological samples. CAO gives us the flexibility to do OCM with known optical aberrations without suffering from the usual resolution penalty that accompanies them. The disclosed OCT technology can utilize hardware AO to deliberately introduce optical system aberrations and acquire N datasets each with a different aberration state (e.g. different angle of astigmatism) to obtain N CAO-OCM reconstructions of the sample scattering potential. If CAO exactly compensates for the induced aberrations, the reconstructed sample structure (resulting from constructive interference of single-scattered light) will be identical across all aberration-diverse datasets. However, given that the 3D shape of the OCM beam changes for different aberration states, the path that the beam travels through the scattering sample will be different, resulting in a randomization of the phase of multiply-scattered contributions across the aberration-diverse CAO-OCM datasets. By performing a coherent sum across aberration-diverse CAO-OCM reconstructions, the single-scattered contribution may add up constructively (i.e. in phase) but the multiply scattered component may add up in random phase; thus increasing (single-scattered) signal to (multiply-scattered) background ratio. Various embodiments of the disclosed technology can be demonstrated in highly scattering tumor spheroids in vitro, and mouse brain ex vivo and in vivo.

The disclosed OCT technology can be used to expand the speed and imaging depth limits of two of widely used optical imaging modalities, OCT and multiphoton microscopy based on aberration diversity in OCT illumination or optical probing and computational adaptive optics (CAO).

This disclosed OCT technology is significant because it targets one of the grand challenges of modern optical microscopy—the detrimental impact of wavefront aberrations on optical imaging resolution, signal-to-noise ratio (SNR) and signal-to-background ratio (SBR). The disclosed OCT technology represents for the first time an integrated approach that combines both HAO and CAO in a complementary fashion to address the impact that aberrations have on speed and imaging depth, for OCT and 3PM, which are the two leading optical modalities for doing deep-tissue in vivo imaging. The disclosed OCT technology can be transformative because it synergistically combines two of the most promising approaches to address the challenge of wavefront aberrations (HAO and CAO) that, to date, have largely been utilized as mutually exclusive methods. Furthermore, the anticipated new imaging capabilities that are developed will be leveraged to launch new avenues of investigation in Mechanobiology and Neuroscience. These include studies on inter-cell coordination of traction forces during 3D migration, and the spatiotemporal patterns of volumetric neural network activity in the mouse brain.

Aberrations and Hardware Adaptive Optics

Aberrations are deviations from an ideal optical wavefronts. These wavefront distortions disrupt the constructive interference that is required to form a sharp optical focus. This significantly degrades the SNR, resolution and imaging depth in optical microscopy. The adaptive optics (AO) has been implemented in microscopy for aberration corrections in a number of optical imaging modalities. For example, an AO method using objective back pupil segmentation has been developed and used to correct for aberrations in a variety of MPM imaging applications. The AO applied in two-photon achieved a significant increase (e.g., about 8×) in signal level when imaging down to 0.4 mm below the surface of brain. The impact of the AO for increasing signal generation is expected to be significantly higher for 3PM because the higher order nonlinear process is much more sensitive to the quality of the focus, provided the required aberration correction (which is sample and depth-dependent) can be determined within the time constraints of the imaging application. Since wavefront distortions accumulate with optical propagation into a heterogeneous biological sample, obtaining diffraction-limited imaging deeper into scattering tissue requires the correction of higher order aberrations. Optical scattering also increases the challenges of sensing aberrations, by requiring time-consuming iterative procedures. In MPM, this problem is compounded by the fact that signal photons are significantly reduced for deeper imaging.

Optical Coherence Tomography and Computational Adaptive Optics

Optical coherence tomography (OCT) is a high-resolution medical and biological imaging technology that is analogous to ultrasound imaging, except that it uses broadband (low-coherence) optical interferometry to precisely localize the position of "echoes" of light. Since OCT systems measure both the amplitude and phase of backscattered light, computational image formation methods have been developed to address traditional limitations in the field of optical imaging, such as the limited depth-of-field, and the detrimental impact of optical aberrations.

Figure 3:
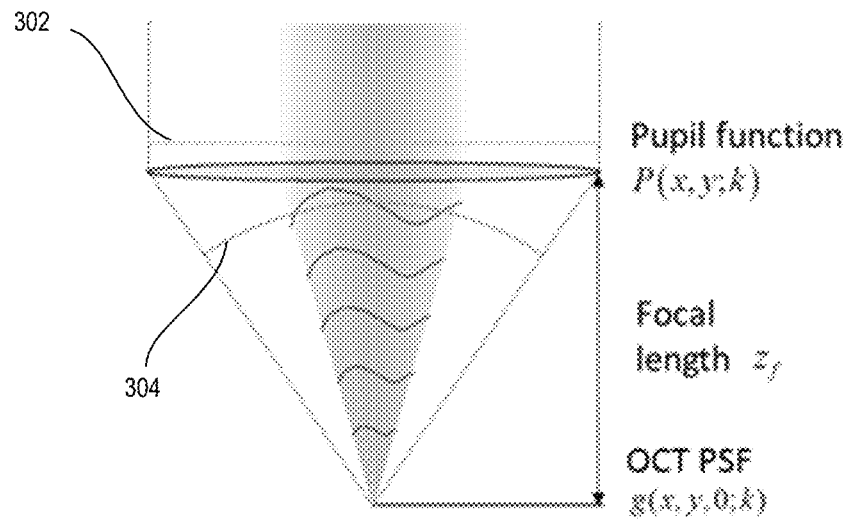
FIG. 3 shows optical aberrations, and the relationship between the computed pupil modified by CAO and the objective lens pupil function that is modified by hardware AO.

FIG. 3 shows optical aberrations, and the relationship between the computed pupil modified by CAO and the objective lens pupil function that is modified by hardware AO, presenting an overview of the capabilities of computed imaging methods in OCT. Optical aberrations are the deviations from ideal wavefronts (see lines labeled 302 and 304). The OCT point-spread function (PSF) is related to the objective pupil function (manipulated by hardware AO) via a Fourier transform. Thus the (double pass) pupil function that CAO numerically modifies the Fourier domain of the reconstructed OCT image is equivalent (neglecting a simple coordinate scaling) to the pupil function that is manipulated by hardware AO.

These computational methods are applicable in highly scattering tissues, including in highly dynamic living systems such as the human eye, providing cellular-resolution imaging of retinal photoreceptors with quality that is comparable to that obtained with hardware AO.

The OCT combining hardware adaptive optics (HAO) and computational adaptive optics (CAO) implemented based on some embodiments of the disclosed technology may include a computational adaptive optics, which is a post-data-acquisition method to compensate both defocus and optical aberration artifacts in the OCT. The method can enable cellular-resolution volumetric imaging in tissue phantoms, highly scattering biological tissue ex vivo or in vivo, and in highly dynamic living systems such as the human retina. CAO is an advance over a previous computed imaging method, interferometric synthetic aperture microscopy (ISAM), which provided the ability to compensate defocus throughout volumetric OCT datasets. CAO is analogous to hardware AO because both techniques manipulate the Fourier domain of the final optical image, and so can be viewed as alternative (although not equivalent) paths to diffraction-limited optical image formation. Indeed, when hardware AO physically modifies the optical wavefront at the objective lens (i.e. modifies the 'pupil function'), this operation directly manipulates the Fourier domain of the physically formed optical image. Analogously, CAO numerically modifies the Fourier domain of the reconstructed OCT image (i.e. it numerically modifies the "computed pupil function," which is also the 3D coherent transfer function or "CTF").

Figure 4:
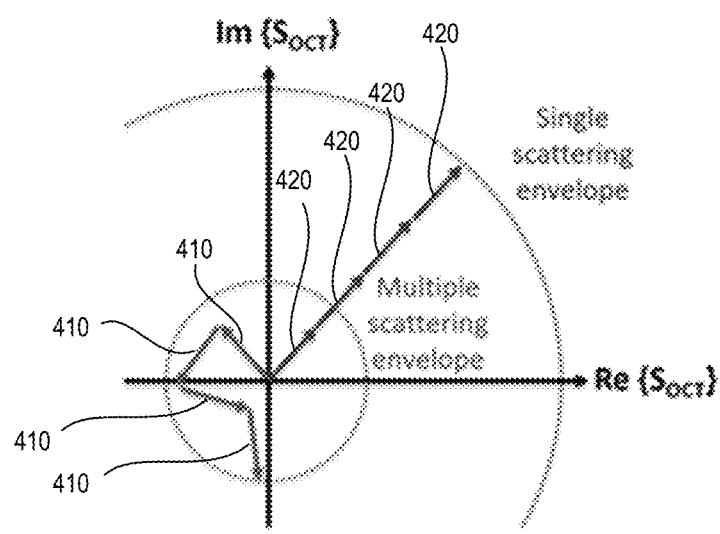
FIG. 4 shows a principle of aberration diverse-computational adaptive optics-optical coherence microscopy (AD-CAO-OCM) approach for suppressing the multiple scattering contribution to the OCT signal.

FIG. 4 shows a principle of aberration diverse-computational adaptive optics-optical coherence microscopy (AD-CAO-OCM) approach for suppressing the multiple scattering contribution to the OCT signal. The OCT signal, $S_{OCT}$, for a given spatial location within a 2D or 3D dataset is shown in the complex plane, with a (single measurement) signal-to-background ratio (SBR) of unity. The single-scattering contribution is shown as arrows labeled with 420 and the multiple scattering contribution to the OCT signal is shown as arrows labeled with 410 (note that all arrows are the same length for SBR=1). After the rapid acquisition of N datasets using different aberration states of the OCT beam, on average the CAO-corrected single scattered contribution will be in phase, but it is postulated that the multiple scattering contributions will have a random phase distribution. The optical wavefront phase is extremely sensitive to light-tissue interactions, and so sufficient variation in the aberration state of the OCT beam is expected to perturb these light-tissue interactions to produce randomly phased multiple scattering contributions. After coherent summation of the CAO-OCM signal over the various aberration states, the single scattered component is seen to jump out from the multiple scattering background. Depending on the number of acquired aberration states, more than an order of magnitude increase in SBR is possible.

Aberration diversity CAO-OCM leverages a coherent accumulation of single scattering (CASS) principle recently demonstrated for enhancing the ratio of the single scattering signal to the multiple scattering background in wide-field coherent microscopy. The approach utilizes the conservation of "in-plane momentum" across acquisition from multiple angles of illumination to constructively add single scattering signals, while adding multiply scattered signals in random phase. If CAO exactly compensates for hardware AO-induced aberrations, the reconstructed CAO-OCM sample structure (resulting from constructive interference of single-scattered light) will be identical across all aberration-diverse datasets, and thus the underlying principle of CASS can be used for a beam-scanned OCT/OCM system to enhance the OCT/OCM imaging quality (see FIG. 4)

The disclosed OCT technology can be used for "super-deep" OCT imaging based on a hybrid adaptive optics implementation of the underlying coherent summation and may be implemented to surpass the multiple scattering limit. In order to estimate the imaging depth in mouse brain that is supported by this coherent summation approach, the Mie scattering model may be utilized. The following table lists the imaging depth predictions at 3 different wavelengths of interest.

| Wavelength (nm) | $\mu_s$ (mm$^{-1}$) | $\mu_s'$ (mm$^{-1}$) | $1/\mu_s$ (mm) | Predicted depth (mm) |
|---|---|---|---|---|
| 800 | 6.9 | 0.68 | 0.14 | 1.7 [Range: 1-3.5] |
| 1300 | 2.7 | 0.50 | 0.38 | 4.3 [Range: 2-8] |
| 1700 | 1.5 | 0.39 | 0.68 | 7.9 [Range: 3-15] |

In an embodiment of the disclosed technology, the OCT system may be implemented using a cylindrical lens combined with a rotational stage or a translational mount. In another embodiment of the disclosed technology, the OCT system may be implemented using a method for switching the illumination aberration state via an adaptive metalens, which provides electrical control of focal length, astigmatism, and shift (beam scanning). In yet another embodiment of the disclosed technology, the OCT system may be implemented using acousto-optic deflectors.

In some embodiments of the disclosed technology, the OCT system may be implemented using a method for switching the illumination aberration state via an adaptive metalens. Flat lens technology based on metasurfaces, which control the wavefront of light using subwavelength-spaced nanostructures, has shown considerable potential in optical performance while reducing element thickness to the micrometer level, opening up new opportunities to replace bulk optical devices with thin, flat, lightweight devices. Instead of moving several optical components longitudinally along the optical axis as in telephoto lenses and autofocus cameras, in metasurfaces, lateral control can be used to vary focus and magnification, as well as other adaptive optics capabilities, and to leverage their flatness. In some implementations, mechanically tunable metasurfaces may include metasurfaces that is embedded in stretchable substrates but is limited in size (less than a millimeter in diameter), required external apparatuses to apply strain, and has inherent speed limitations, restricting their applications. The combination of metasurface optics and dielectric elastomer actuators (DEAs) can offer a versatile platform for electrically tunable optical devices through the design of phase, amplitude, and polarization profiles.

A polarization-insensitive, converging metalens may be combined with a DEA constructed using transparent polyacrylate elastomers with transparent, stretchable patterned electrodes made of single-walled carbon nanotubes. Any combination of actuations, each implemented using different voltages, may also be possible.

In some embodiments of the disclosed technology, the OCT system may be implemented using acousto-optic deflectors. Acousto-optic lenses (AOLs) allow rapid, inertia-free focusing and scanning of an optical beam. The AOLs may be implemented in the hybrid OCT system based on some embodiments of the disclosed technology. The AOLs are well suited for this application because they allow spatially distributed points of interest to be monitored.

In some example implementations, the AOLs may use pairs of acousto-optic deflectors (AODs) to focus and deflect an optical beam. The AODs in each pair are oppositely orientated such that their acoustic waves are counter-propagating in space. A single pair of AODs can form a cylindrical AOL and an orthogonal pair of cylindrical AOLs form a spherical AOL. Focusing is achieved by driving the transducers of the AODs with linearly-chirped frequencies, while beam steering is achieved by offsetting the frequency.

In some embodiments of the disclosed technology, a deformable mirror (DM) may be used to switch aberration states. Other methods for switching aberration states include using a spatial light modulator, or a digital micromirror device (DMD).

Figure 5:
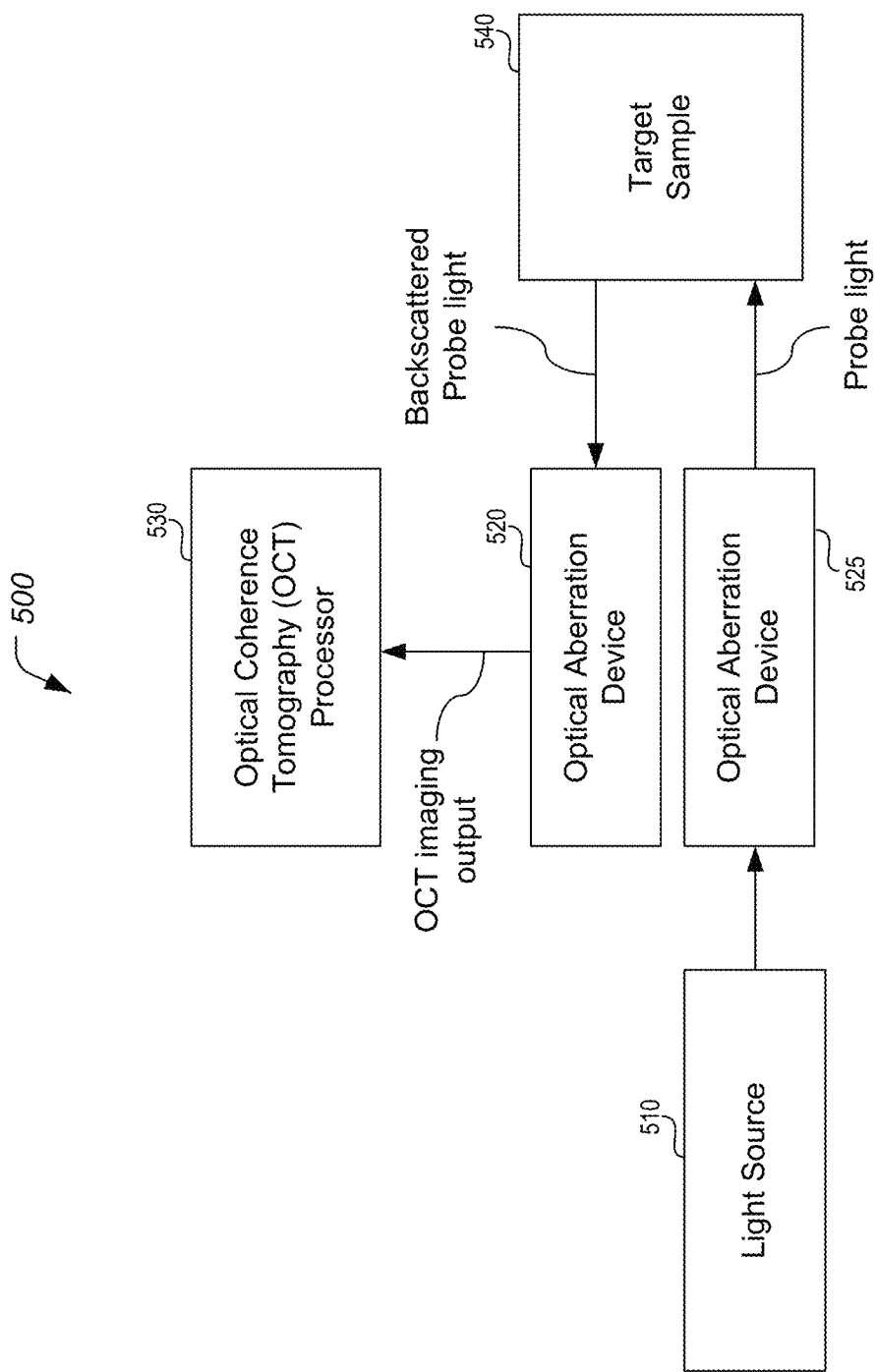
FIG. 5 shows an example of OCT system implemented based on some embodiments of the disclosed technology

FIG. 5 shows an example of OCT system implemented based on some embodiments of the disclosed technology. The optical coherence tomography (OCT) system 500 may include a light source 510, and optical aberration devices 520 and 525, and an OCT processor 530. The light source 510 for OCT imaging may be designed to have a relatively short temporal coherence length, e.g., smaller than or at the order of 1 μm. The light source 510 is configured to direct probe light to the target sample through the optical aberration device 525 to collect returned probe light from the target sample to perform OCT imaging. The optical aberration device 520 is placed in an optical path of backscattered probe light from the target sample and structured to sequentially superimpose different optical aberration patterns on the wavefront of the probe light directed to the target sample to obtain different OCT imaging outputs, respectively, that respectively correspond to the different optical aberration patterns. The OCT processor 530 is coupled to the optical aberration device to receive the different OCT imaging outputs that respectively correspond to the different optical aberration patterns and to process the received different OCT imaging outputs to reconstruct different OCT images of the target sample, respectively, where each reconstructed OCT image corresponds to one of the different OCT imaging outputs and includes (1) first OCT image components that are caused by ballistic photons of the probe light with a single-scattering contribution and are in phase and (2) second OCT image components that are caused by scattered photons of the probe light due to scattering in the target sample and exhibit random phase values. The OCT processor is further configured to add the reconstructed OCT images together to obtain a final reconstructed OCT image based on a first sum of the first OCT image components of the different reconstructed OCT images that are in phase and a second sum of the second OCT image components of the different reconstructed OCT images exhibiting random phase values, thus suppressing a contribution of the second sum caused by scattered photons of the probe light due to scattering in the target sample.

The optical aberration device includes a rotating lens to produce a varying optical lens astigmatism that in turn produces the different optical aberration patterns. The optical aberration device includes at least one of an adaptive optical device, a deformable mirror, an adaptive metalens equipped with electrical control of a focal length, lens astigmatism, and beam scanning, an acoustic deflector, and a deformable digital mirror array. The OCT system may be structured based on spectral or frequency domain OCT.

In some implementations, the optical aberration device includes multiple stages of aberration control that are combined in such a way that each separate stage can be used to control/induce different magnitude of aberrations. One embodiment is a two-stage method, with one device controlling/inducing aberrations of large magnitude, and another device to separately control/induce small, precise aberrations.

Figure 6:
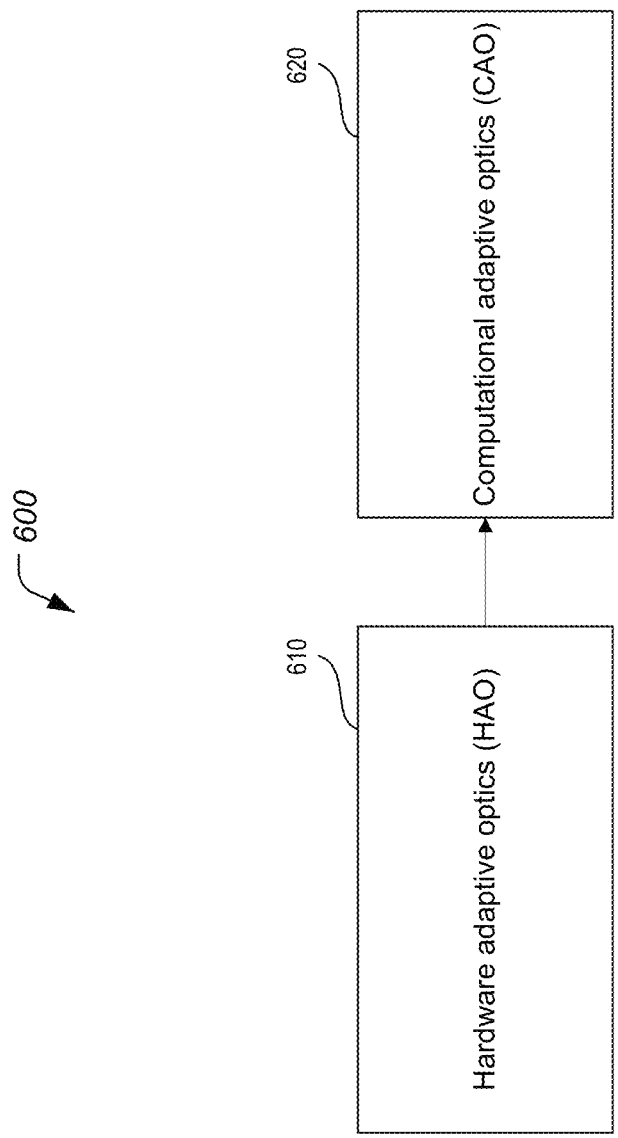
FIG. 6 shows an example of an aberration control OCT system implemented based on some embodiments of the disclosed technology.

FIG. 6 shows an example of an aberration control OCT system 600 implemented based on some embodiments of the disclosed technology. The aberration control OCT system 600 may include hardware adaptive optics (HAO) 610 to introduce an astigmatic wavefront aberration and computational adaptive optics (CAO) 620 to undo this aberration during post-processing. For example, the HAO 610 may be used to acquire N datasets with different aberration states from a sample by introducing different optical aberrations, and the CAO 620 may be used to obtain N aberration-diverse CAO-OCM reconstructions and undo the aberration by performing a coherent sum across the N aberration-diverse CAO-OCM reconstructions.

Figure 7:
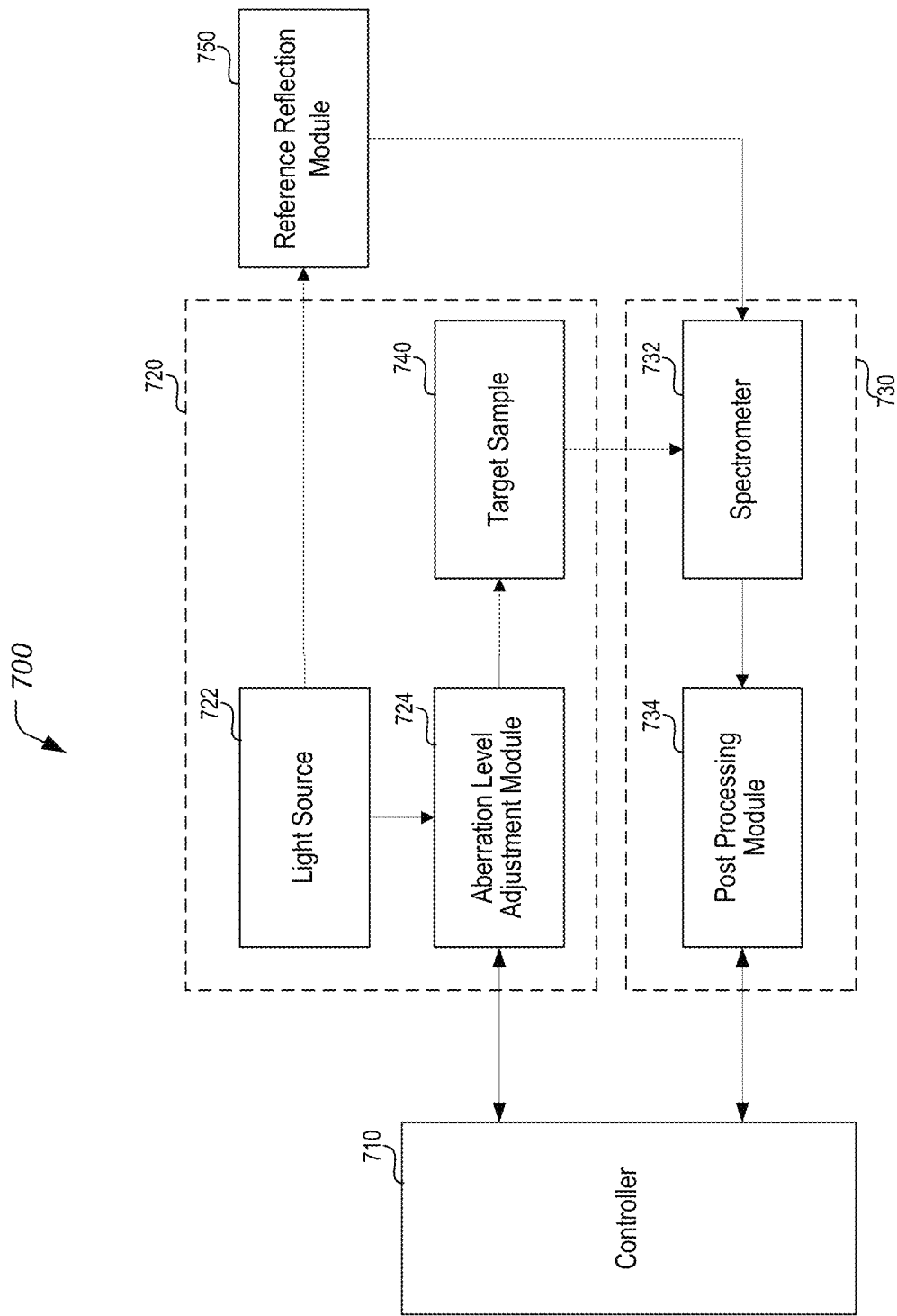
FIG. 7 shows an example configuration of the OCT system based on some embodiments of the disclosed technology.

FIG. 7 shows an example configuration of the OCT system 700 based on some embodiments of the disclosed technology. The hybrid OCT system 700 may include a controller 710, a HAO 720, a CAO 730, and a reference reflection module 750. The HAO 720 may include a light source 722, an aberration level adjustment module 724 (e.g., astigmatism level), and a target sample stage 740. The CAO 730 may include a spectrometer 732 and a post processing module 734.

In some embodiments of the disclosed technology, the aberration level adjustment module 724 may include one or more deformable mirrors to physically adjust the aberration level and the corresponding separation distance between line foci. In an implementation, a single axial beam position is used to acquire an OCM volume with desired depth coverage. In another implementation, an additional amount of defocus can be applied to the deformable mirror to acquire multiple datasets with the plane of least confusion at different depths by shifting the nominal focus. The multiple datasets include a number of volumetric OCT measurements taken with an astigmatic interrogating beam.

In some embodiments of the disclosed technology, the aberration level adjustment module 724 may include an adaptive metalens structure to switch the illumination aberration state. In an implementation, the adaptive metalens structure may include metasurface optics and dielectric elastomer actuators. In some embodiments of the disclosed technology, the aberration level adjustment module 724 may include acousto-optic deflectors to adjust the aberration level.

In an embodiment of the disclosed technology, the reference reflection module 750 may be implemented as an arm that is separate from the target sample stage 740. In another embodiment of the disclosed technology, the reference reflection module 750 may be implemented as a "common-path" with an arm including the target sample stage 740.

Figure 8:
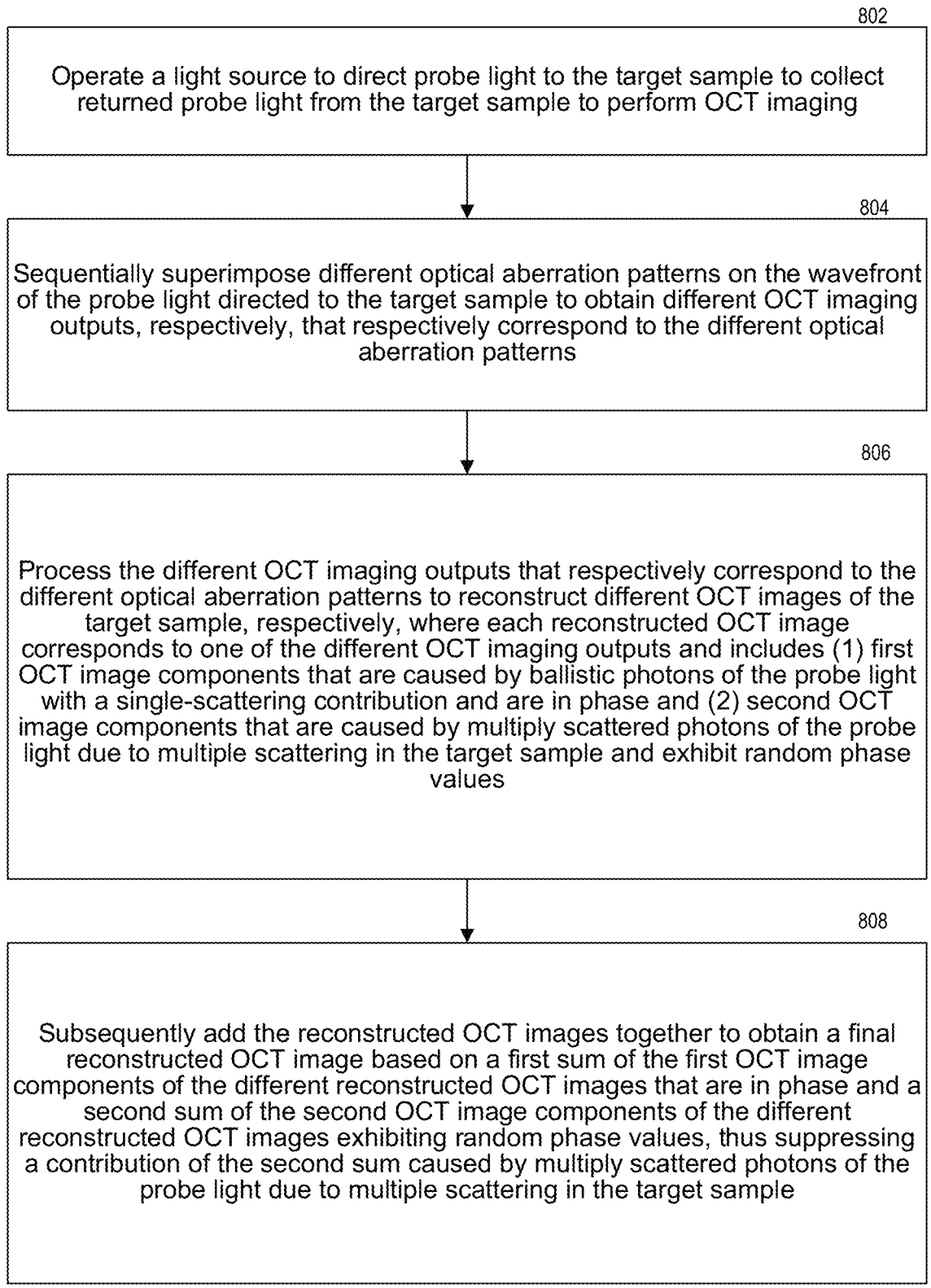
FIG. 8 shows an example method for optically measuring a target sample based on optical coherence tomography (OCT) imaging.

FIG. 8 shows an example method for optically measuring a target sample based on optical coherence tomography (OCT) imaging. The method may include, at step 802, operating a light source to direct probe light to the target sample and to collect returned probe light from the target sample to perform OCT imaging, at step 804, sequentially superimposing different optical aberration patterns on the wavefront of the probe light directed to the target sample to obtain different OCT imaging outputs, respectively, that respectively correspond to the different optical aberration patterns, at step 806, processing the different OCT imaging outputs that respectively correspond to the different optical aberration patterns to reconstruct different OCT images of the target sample, respectively, where each reconstructed OCT image corresponds to one of the different OCT imaging outputs and includes (1) first OCT image components that are caused by ballistic photons of the probe light with a single-scattering contribution and are in phase and (2) second OCT image components that are caused by multiply scattered photons of the probe light due to multiple scattering in the target sample and exhibit random phase values, and, at step 808, subsequently adding the reconstructed OCT images together to obtain a final reconstructed OCT image based on a first sum of the first OCT image components of the different reconstructed OCT images that are in phase and a second sum of the second OCT image components of the different reconstructed OCT images exhibiting random phase values, thus suppressing a contribution of the second sum caused by multiply scattered photons of the probe light due to multiple scattering in the target sample.

In some implementations, the step of sequentially superimposing different optical aberration patterns on the wavefront of the probe light directed to the target sample may be performed by using a rotating lens to produce a varying optical lens astigmatism. The step of sequentially superimposing different optical aberration patterns on the wavefront of the probe light directed to the target sample may be performed by using an adaptive optical device. The step of sequentially superimposing different optical aberration patterns on the wavefront of the probe light directed to the target sample may be performed by using a deformable mirror. The step of sequentially superimposing different optical aberration patterns on the wavefront of the probe light directed to the target sample may be performed by using an adaptive metalens equipped with electrical control of a focal length, lens astigmatism, and beam scanning. The step of sequentially superimposing different optical aberration patterns on the wavefront of the probe light directed to the target sample may be performed by using an acoustic deflector. The step of sequentially superimposing different optical aberration patterns on the wavefront of the probe light directed to the target sample may be performed by using a deformable digital mirror array. In some implementations, the optical coherence tomography (OCT) imaging is based on spectral or frequency domain OCT.

In some implementations, the optical aberration device may include a rotating lens to produce a varying optical lens astigmatism that in turn produces the different optical aberration patterns. The step of sequentially superimposing different optical aberration patterns on the wavefront of the probe light directed to the target sample may be performed by a multi-stage process, in which large lower order aberration and small higher order aberration can be applied separately. The multi-stage process may be performed by using a combination of a cylindrical lens and a wavefront shaping device including at least one of an adaptive optical device, a deformable mirror, an adaptive metalens, an acoustic deflector, and a deformable digital mirror array. the cylindrical lens is used for introducing large astigmatism, and the wavefront shaping device is used for making precise perturbations to the level of astigmatism, and/or implementing aberration control of non-astigmatic aberrations, and/or overcoming aberrations introduced by the sample itself.

Figure 9:
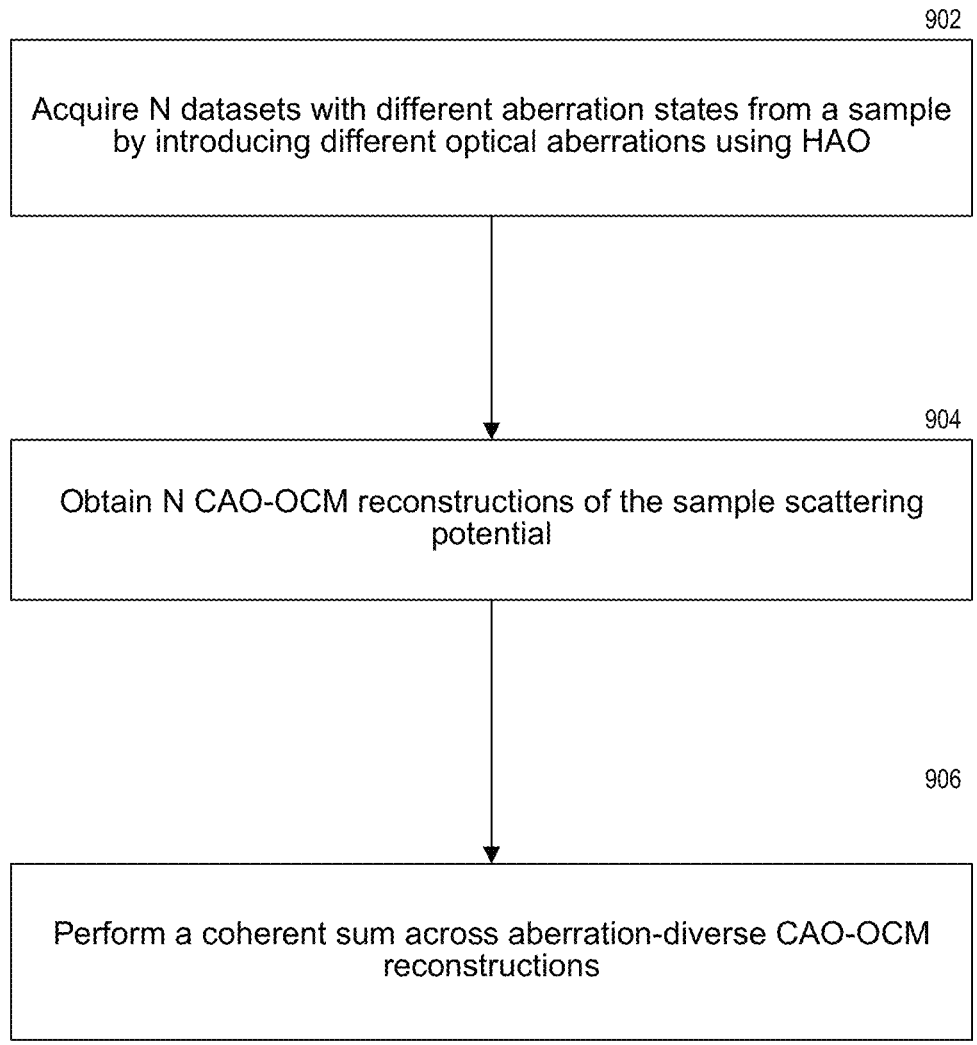
FIG. 9 shows an example of optical coherent tomography (OCT) imaging method based on some embodiments of the disclosed technology.

FIG. 9 shows another example of optical coherent tomography (OCT) imaging method based on some embodiments of the disclosed technology. The method may include, at step 902, acquiring N datasets with different aberration states from a sample by introducing different optical aberrations using HAO, at step 904, obtaining N CAO-OCM reconstructions of the sample scattering potential, and, at step 906, performing a coherent sum across aberration-diverse CAO-OCM reconstructions.

Although a few variations have been described in detail above, other modifications or additions are possible. In particular, further features and/or variations may be provided in addition to those set forth herein. Moreover, the example embodiments described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. Other embodiments may be within the scope of the following claims.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document. It should be noted, that this approach can also include modulators integrated on the same chip in support of such applications as digital communications, RF photonics, and LIDAR Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for optically measuring a target sample based on Optical Coherence Tomography (OCT) imaging, comprising:
   operating a light source to direct probe light to a location of the target sample to collect returned probe light from the location of the target sample to perform OCT imaging;
   sequentially superimposing different optical aberration patterns on the wavefront of the probe light directed to the location of the target sample to obtain different OCT imaging outputs of the location of the target sample, respectively, that respectively correspond to the different optical aberration patterns;
   processing the different OCT imaging outputs that respectively correspond to the different optical aberration patterns to reconstruct different OCT images of the location of the target sample, respectively, where each reconstructed OCT image corresponds to one of the different OCT imaging outputs and includes (1) first OCT image components that are caused by ballistic photons of the probe light with a single-scattering contribution and are in phase and (2) second OCT image components that are caused by multiply scattered photons of the probe light due to multiple scattering in the target sample and exhibit random phase values; and
   subsequently adding the reconstructed OCT images together to obtain a final reconstructed OCT image based on a first sum of the first OCT image components of the different reconstructed OCT images that are in phase and a second sum of the second OCT image components of the different reconstructed OCT images exhibiting random phase values, thus suppressing a contribution of the second sum caused by multiply scattered photons of the probe light due to multiple scattering in the target sample,
   wherein the first and second OCT image components include complex valued OCT signals.

2. The method as in claim 1, wherein:
   the step of sequentially superimposing different optical aberration patterns on the wavefront of the probe light directed to the target sample is performed by using a rotating lens to produce a varying optical lens astigmatism.

3. The method as in claim 1, wherein:
   the step of sequentially superimposing different optical aberration patterns on the wavefront of the probe light directed to the target sample is performed by using an adaptive optical device.

4. The method as in claim 1, wherein:
   the step of sequentially superimposing different optical aberration patterns on the wavefront of the probe light directed to the target sample is performed by using a deformable mirror.

5. The method as in claim 1, wherein:
   the step of sequentially superimposing different optical aberration patterns on the wavefront of the probe light directed to the target sample is performed by using an adaptive metalens structured to provide electrical control of a focal length, lens astigmatism, and beam scanning.

6. The method as in claim 1, wherein:
   the step of sequentially superimposing different optical aberration patterns on the wavefront of the probe light directed to the target sample is performed by using an acoustic deflector.

7. The method as in claim 1, wherein:
   the step of sequentially superimposing different optical aberration patterns on the wavefront of the probe light directed to the target sample is performed by using a deformable digital mirror array.

8. The method as in claim 1, wherein:
   the OCT imaging is based on spectral or frequency domain OCT.

9. The method as in claim 1, wherein sequentially superimposing different optical aberration patterns includes rotating lens to produce the different optical aberration patterns.

10. The method as in claim 1, wherein the step of sequentially superimposing different optical aberration patterns on the wavefront of the probe light directed to the target sample is performed by a multi-stage process, in which large lower order aberration and small higher order aberration can be applied separately.

11. The method as in claim 10, wherein the multi-stage process is performed by using a combination of a cylindrical lens and a wavefront shaping device including at least one of an adaptive optical device, a deformable mirror, an adaptive metalens, an acoustic deflector, and a deformable digital mirror array.

12. An optical coherent tomography (OCT) device for optically measuring a target sample, comprising:
   a light source to direct probe light to a location of the target sample to collect returned probe light from the location of the target sample to perform OCT imaging;
   an optical aberration device placed in an optical path of the returned probe light from the target sample and structured to sequentially superimpose different optical aberration patterns on the wavefront of the probe light directed to the location of the target sample to obtain different OCT imaging outputs of the location of the target sample, respectively, that respectively correspond to the different optical aberration patterns;

an OCT processor coupled to the optical aberration device to receive the different OCT imaging outputs that respectively correspond to the different optical aberration patterns and to process the received different OCT imaging outputs to reconstruct different OCT images of the location of the target sample, respectively, where each reconstructed OCT image corresponds to one of the different OCT imaging outputs and includes (1) first OCT image components that are caused by ballistic photons of the probe light with a single-scattering contribution and are in phase and (2) second OCT image components that are caused by scattered photons of the probe light due to scattering in the target sample and exhibit random phase values, wherein the OCT processor is further configured to add the reconstructed OCT images together to obtain a final reconstructed OCT image based on a first sum of the first OCT image components of the different reconstructed OCT images that are in phase and a second sum of the second OCT image components of the different reconstructed OCT images exhibiting random phase values, thus suppressing a contribution of the second sum caused by scattered photons of the probe light due to scattering in the target sample, wherein the first and second OCT image components include complex valued OCT signals.

13. The OCT device as in claim 12, wherein:
the optical aberration device includes a rotating lens to produce a varying optical lens astigmatism that in turn produces the different optical aberration patterns.

14. The OCT device as in claim 12, wherein:
the optical aberration device includes an adaptive optical device.

15. The OCT device as in claim 12, wherein:
the optical aberration device includes a deformable mirror.

16. The OCT device as in claim 12, wherein:
the optical aberration device includes an adaptive metalens structured to provide electrical control of a focal length, lens astigmatism, and beam scanning.

17. The OCT device as in claim 12, wherein:
the optical aberration device includes an acoustic deflector.

18. The OCT device as in claim 12, wherein:
the optical aberration device includes a deformable digital mirror array.

19. The OCT device as in claim 12, wherein:
the OCT device is structured based on spectral or frequency domain OCT.

20. The OCT device as in claim 12, wherein:
the optical aberration device includes multiple stages of aberration control including one stage to control and induce aberrations of large magnitude and another stage to separately control and induce small, precise aberrations.

* * * * *